United States Patent [19]

Theeuwes et al.

[11] Patent Number: 5,250,028

[45] Date of Patent: * Oct. 5, 1993

[54] INTRAVENOUS SYSTEM FOR DELIVERING A BENEFICIAL AGENT USING PERMEABILITY ENHANCERS

[75] Inventors: Felix Theeuwes; Su I. Yum, both of Los Altos, Calif.

[73] Assignee: ALZA Corporation, Palo Alto, Calif.

[ * ] Notice: The portion of the term of this patent subsequent to Jan. 15, 2008 has been disclaimed.

[21] Appl. No.: 741,477

[22] Filed: Aug. 9, 1991

Related U.S. Application Data

[63] Continuation-in-part of Ser. No. 311,905, Feb. 15, 1989, Pat. No. 4,985,016.

[51] Int. Cl.⁵ .............................................. A61M 37/00
[52] U.S. Cl. ........................................ 604/85; 604/56; 604/82; 604/892.1
[58] Field of Search ................................ 604/80–85, 604/890.1, 56, 892.1

[56] References Cited

U.S. PATENT DOCUMENTS

| | | | |
|---|---|---|---|
| 3,536,809 | 10/1970 | Applezweig | 424/28 |
| 3,598,122 | 8/1971 | Zaffaroni | 128/268 |
| 3,598,123 | 8/1971 | Zaffaroni | 128/268 |
| 3,699,963 | 10/1972 | Zaffaroni | 128/268 |
| 3,726,276 | 4/1973 | Schumann et al. | 128/227 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,787,571 | 1/1974 | Higuchi | 424/239 |
| 3,788,316 | 1/1974 | Mora | 128/200 |
| 3,964,482 | 6/1976 | Gerstel et al. | 128/260 |
| 3,996,934 | 12/1976 | Zaffaroni | 128/268 |
| 4,031,894 | 6/1977 | Urquhart et al. | 128/268 |
| 4,060,084 | 11/1977 | Chandrasekaran et al. | 128/260 |
| 4,144,317 | 3/1979 | Higuchi et al. | 424/21 |
| 4,479,793 | 10/1984 | Urquhart et al. | 604/85 |
| 4,511,353 | 4/1985 | Theeuwes | 604/85 |
| 4,533,348 | 8/1985 | Wolfe et al. | 604/85 |
| 4,552,555 | 11/1985 | Theeuwes | 604/56 |
| 4,606,734 | 8/1986 | Larkin et al. | 604/84 |
| 4,664,650 | 5/1987 | Urquhart et al. | 604/85 |
| 4,669,458 | 6/1987 | Abraham et al. | 128/133 |
| 4,740,103 | 4/1988 | Theeuwes | 604/83 |
| 4,740,200 | 4/1988 | Theeuwes | 604/85 |
| 4,740,201 | 4/1988 | Theeuwes | 604/85 |
| 4,792,450 | 12/1988 | Kydonieus et al. | 424/449 |
| 4,837,027 | 6/1989 | Lee et al. | 424/449 |
| 4,871,352 | 10/1989 | Tron | 604/82 |
| 5,160,320 | 11/1992 | Yum et al. | 604/85 |

FOREIGN PATENT DOCUMENTS

151371 8/1985 European Pat. Off. .
WO8404036 10/1984 PCT Int'l Appl. .

OTHER PUBLICATIONS

J. Pharma Sci., vol. 52, pp. 1145–1149, (1963).
J. Pharma Sci., vol. 53, pp. 798–802, (1964).
J. Pharma Sci., vol. 54, pp. 1459–1464, (1965).
J. Pharma Sci., vol. 55, pp. 840–843 and pp. 1224–1229 (1966).
Encyl. Polymer Sci. Technol., vol. 5, pp. 65–82 and vol. 9, pp. 794–807 (1986).
PCT Search Report, PCT/US90/00871 (This Appl.) (Jun. 6, 1990) Citations included in this IDC.
PCT, International Preliminary Examination Report, PCT/US90/00871 (This Appl.) (May 23, 1991).

*Primary Examiner*—C. Fred Rosenbaum
*Assistant Examiner*—Mark Bockelman
*Attorney, Agent, or Firm*—R. Scott Meece; D. Byron Miller; Edward L. Mandell

[57] ABSTRACT

A drug formulation chamber for an intravenous administration set is provided. The intravenous administration set includes a container of an IV fluid, a drip chamber, a drug formulation chamber, and an adapter-needle assembly. The drug formulation chamber has a fluid inlet and a fluid outlet for maintaining a flow of IV fluid through the chamber. A portion of the chamber wall is comprised of a material which is permeable to the drug but which prevents convective loss of the IV fluid. A transdermal-type drug delivery device is adhered to the semipermeable/microporous wall portion. Drug is delivered by the delivery device through the wall portion using permeation enhancers and into the flowing IV fluid. The device delivers drug into the IV fluid at a rate that is independent of the flow rate of IV fluid through the formulation chamber. The rate of drug delivery from the device into the IV fluid is controlled by either the wall portion or a membrane layer in the drug delivery device. A plurality of drug delivery devices may be adhered to the wall portion to deliver a plurality of drugs or to deliver a single drug at a higher dosage rate.

34 Claims, 1 Drawing Sheet

INTRAVENOUS SYSTEM FOR DELIVERING A BENEFICIAL AGENT USING PERMEABILITY ENHANCERS

This application is a continuation-in-part application of U.S. patent application Ser. No. 311,905 filed Feb. 15, 1989, now U.S. Pat. No. 4,985,016.

This application is related to U.S. patent application Ser. No. 311,905, filed Feb. 15, 1989, now U.S. Pat. No. 4,969,871.

This invention pertains to a parenteral drug delivery system, and to a drug formulation chamber in combination with a drug delivery device. The invention relates also to a method of parenterally (e.g., intravenously) administering a drug, and to a method of formulating the drug during parenteral administration.

BACKGROUND ART

The parenteral administration of medical liquids is an established clinical practice. The liquids are administered particularly intravenously, and the practice is used extensively as an integral part of the daily treatment of medical and surgical patients. The liquids commonly administered include blood and blood substitutes, dextrose solutions, electrolyte solutions and saline. Generally the liquids are administered from an intravenous (IV) delivery system having a container suspended above the patient, with the liquid flowing through a catheter hypodermic needle set to-the patient.

The administration of liquids intravenously is a valuable and important practice that contributes to the optimal care of the patient. However, it does not easily provide a satisfactory means and method for administering concomitantly therewith a beneficial agent, such as a drug. In the past, beneficial agents have been administered intravenously by one of the following methods: (1) temporarily removing or disconnecting the IV system administering the agent to the patient, then administering the drug by hypodermic injection (either into the disconnected IV line or directly into the vein of the patient), followed by reinserting the IV system into the patient; (2) adding the agent to the IV liquid in the container which is then carried by the flow of the liquid to the patient; (3) adding the agent to an IV liquid in a secondary container (called a partial fill) that is then connected to the primary IV line; (4) adding the agent to an IV liquid contained in a piggyback vial which is subsequently connected to the primary IV line; or (5) administering intravenously an IV liquid containing a beneficial agent using a pump. While these techniques are used, they have major disadvantages. For example, they often require preformulation of the agent medication by the hospital pharmacist or nurse. They often require separate connections for joining the drug flow line to the primary intravenous line which further complicates intravenous administration. The use of certain types of pumps (e.g., reciprocating pumps) can produce pressures that can vary at the delivery site. Finally, the rate of agent delivery to the patient often is unknown as it is not rate-controlled agent delivery but rather is dependent on the rate of IV fluid flow.

In response to these difficulties, Theeuwes in U.S. Pat. No. 4,511,353 (and in related U.S. Pat. Nos. 4,740,103; 4,740,200 and 4,740,201) developed a formulation chamber adapted to easily fit into a conventional IV administration set. The formulation chamber is adapted to contain a drug delivery device for delivering a drug or other beneficial agent into the IV fluid flowing through the formulation chamber. The drug delivery device within the formulation chamber is selected from osmotic pumps (FIGS. 2a, 2b, 9, 10, and 11), release rate controlling membranes surrounding a drug reservoir (FIGS. 3-5), rate-controlled delivery reservoirs with a pocket in the drug formulation chamber, the pocket formed by a permeable membrane or screen/mesh which allows passage of both IV fluid and drug solution therethrough (FIGS. 12 and 13) and polymer matrices containing the drug, the drug being able to diffuse through the matrix into the flowing IV fluid (FIGS. 6-8). All of these devices provide the advantage of controlling the rate at which the drug or other beneficial agent is released into the IV fluid, independently of the rate at which the IV fluid flows through the formulation chamber. Unfortunately, the drug delivery systems disclosed in these patents do not allow a medical technician to quickly and easily change the type of beneficial agent being delivered into the flowing IV fluid or to quickly and easily change the delivery rate of the beneficial agent so delivered. In order to change the type of agent delivered or the agent delivery rate with the delivery systems disclosed in these patents, it is necessary to completely disassemble the drug formulation chamber and replace the rate-controlled drug delivery device within the chamber. Unfortunately, when the drug formulation chamber is disassembled, there is a break in the sterile field which can lead to patient infection and therefore necessitates re-sterilizing the entire apparatus.

Thus, there remains a need for a drug formulation chamber which can deliver one or more beneficial agents, such as a drug, into an IV fluid flowing in a standard IV administration set and which can quickly and easily change the type and/or change the delivery rate of beneficial agent so delivered without contaminating the sterile field.

Accordingly, it is an object of this invention to provide a parenteral (e.g., intravenous) delivery system which delivers an agent at a controlled rate into a flowing parenteral fluid for optimizing the care of an animal (e.g., a human) whose prognosis benefits from parenteral delivery.

It is another object of the invention to provide an intravenous delivery system having an agent formulation chamber which is adapted to be used with a drug delivery device for admitting a drug or other beneficial agent at a rate controlled by either the drug delivery device, the formulation chamber, or both, instead of by the flow rate of intravenous fluid through the system, for optimizing the care of a patient on intravenous delivery. Another object of the invention is to provide an intravenous delivery system having an agent formulation chamber which is adapted to be used with a transdermal-type drug delivery device which can deliver one or more beneficial agents, such as a drug, into an IV fluid flowing through the formulation chamber and which can quickly and easily change the type and/or change the delivery rate of beneficial agent so delivered without contaminating the sterile conditions within the drug formulation chamber.

A further object of the invention is to provide an intravenous therapeutic system including a container of an intravenous medical fluid and a drug formulation chamber in combination with a drug delivery device which can deliver drug, to a flowing IV fluid, at a rate which is variable and which is accurately controlled by the components of the system.

DISCLOSURE OF THE INVENTION

These and other objects are met by an agent formulator, a parenteral administration system and a method for the controlled parenteral administration of a beneficial agent to an animal. The agent formulator comprises a chamber having fluid inlet and fluid outlet means to maintain a continuous flow of a parenterally acceptable fluid therethrough. The chamber has a wall portion that is permeable to a beneficial agent to be delivered into the fluid. The beneficial agent should be soluble in the parenteral fluid to enable the agent to diffuse through the wall portion. An agent delivery device is releasably attached to an easily accessible exterior surface of the wall portion. The delivery device includes a reservoir containing the beneficial agent to be delivered into the parenteral fluid. Preferably, the delivery device is a transdermal drug delivery device comprising a laminate including a backing member, a middle reservoir containing the beneficial agent and an adhesive surface adapted to releasably adhere to the exterior surface of the wall portion. Most preferably, the agent delivery device also includes a rate controlling membrane which controls the rate at which the agent is delivered through the wall portion.

In operation, the fluid flowing through the chamber contacts an interior surface of the wall portion, thereby causing the agent to diffuse from the device through the wall portion and into the flowing fluid. The agent is delivered at a rate that is controlled substantially by the formulator and which is substantially independent of the volumetric flow rate of the fluid flowing through the chamber.

The present invention also provides a parenteral delivery system for administering an agent parenterally to an animal. The system comprises in combination, a container of a pharmaceutically acceptable parenteral fluid that is a carrier for the agent and a parenteral fluid administration set. The administration set is connected to the container for permitting the fluid to flow from the container through the administration set to the animal. The administration set comprises a drip chamber, tubing extending from the drip chamber to the animal, and an agent formulator connected into the tubing such that the intravenous fluid flows through the formulator. The formulator includes a chamber having fluid inlet and outlet means to maintain a continuous flow of the parenteral fluid therethrough. The chamber has a wall portion that is permeable to a beneficial agent to be delivered into the fluid. The beneficial agent should be soluble in the parenteral fluid to enable the agent to diffuse through the wall portion. The formulator also includes an agent delivery device releasably attached to an easily accessible external surface of the wall portion. The delivery device includes a reservoir containing the beneficial agent to be delivered. Preferably, the delivery device is a transdermal drug delivery device comprising a laminate including a backing member, a middle reservoir containing the beneficial agent and an adhesive surface adapted to releasably adhere to the external surface of the wall portion. Most preferably, the agent delivery device includes a rate controlling membrane which controls the rate at which the agent is delivered through the wall portion.

In operation, the fluid flowing through the chamber contacts an internal surface of the wall portion, causing the agent to diffuse from the device through the wall portion and into the flowing fluid. The agent is delivered at a rate which is controlled substantially by the formulator and which is substantially independent of the volumetric flow rate of the fluid flowing through the chamber.

The present invention further provides a method for the controlled parenteral administration of a beneficial agent, such as a drug, to an animal, such as a human. The method comprises the steps of admitting into the animal a parenteral fluid administration system. The system includes a container of a pharmaceutically acceptable parenteral fluid that is a carrier for the agent and an agent formulation chamber. The chamber has an inlet that communicates with the container to permit the fluid to flow from the container into the chamber and an outlet that communicates with the animal to permit the fluid to flow from the chamber into the animal. The chamber also has a wall portion that is permeable to the agent. The method further comprises the step of releasably attaching an agent delivery device to an exterior surface of the wall portion. The delivery device includes a reservoir containing the beneficial agent to be delivered. Preferably, the delivery device is a transdermal drug delivery device comprising a laminate including a backing member, a middle reservoir containing the beneficial agent and an adhesive surface adapted to releasably adhere to the external surface of the wall portion. Most preferably, the agent delivery device includes a rate controlling membrane which controls the rate at which the agent is delivered through the wall portion.

In operation, the fluid flowing through the chamber contacts an interior surface of the wall portion, causing the agent to diffuse from the device through the wall portion and into the flowing fluid. The agent is released at a rate which is controlled substantially by the delivery device or by the wall portion and which is substantially independent of the volumetric flow rate of the fluid flowing through the chamber. The method is effective to administer the drug/agent to the animal in a beneficially effective amount over a prolonged period of time.

BRIEF DESCRIPTION OF THE DRAWINGS

In the specification and the drawings, like parts in related Figures are identified by like numbers.

MODES FOR CARRYING OUT THE INVENTION

Figure 1:
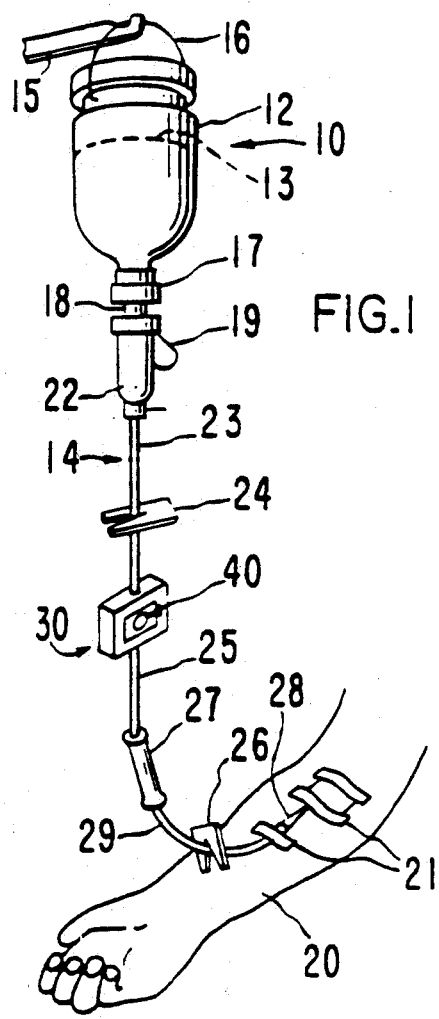
FIG. 1 is a perspective view showing an agent formulator 30 and its use within an intravenous delivery system 10.

FIG. 1 illustrates an operative intravenous delivery system, generally designated by the numeral 10, showing the positioning of an agent formulator 30 therein. System 10 comprises a container 12 that contains a fluid 13 suitable for intravenous administration, and an administration set, generally designated 14. The fluid 13 in container 12 will typically be a medical fluid, i.e., a sterile solution such as an aqueous solution of dextrose, saline, and/or electrolytes. Fluid 13 is a vehicle for intravenous administration of a pharmaceutical agent to a recipient. Container 12 is manufactured from glass or plastic, and is preferably of the no air-tube vacuum type and thus it is used with an administration set that has an air inlet filter. Other types of containers such as the air-tube vacuum type, or the non-vented type, can be used for the intended purpose. These alternative containers do not require an air filter in the administration set. Container 12 can be rigid, semi-rigid or flexible in structure, and it is usually adapted to be hung neck-down from a hanger 15 by a handle 16 that connects or surrounds container 12. The neck of container 12 is covered by a closure 17, generally made of rubber and air-tight.

Alternatively, container 12 can take the form of an infusor or a syringe pump (not shown in the Figures), and in particular a portable infusor or syringe pump, of the kind known in this art.

Figure 2:
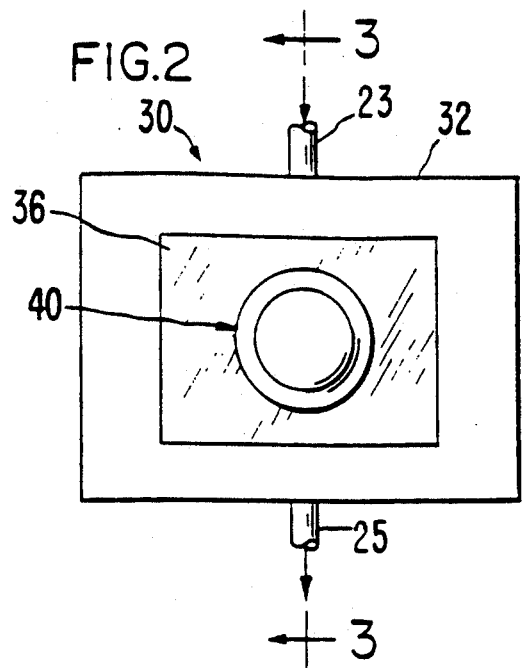
FIG. 2 is a sectional view of one embodiment of an agent formulator according to the present invention.
Figure 3:
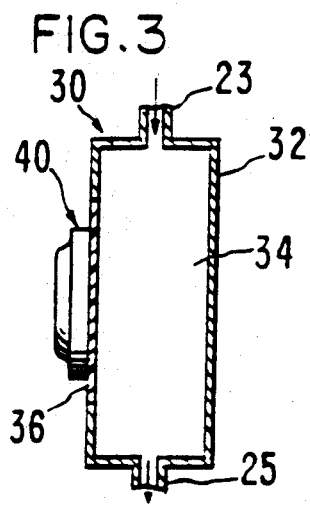
FIG. 3 is a sectional view of the agent formulator illustrated in FIG. 2, taken along line 3—3.

Administration set 14 and container 12 are interconnected by piercing closure 17 with one end of a hollow spike 18 attached to or formed as a part of administration set 14. Spike 18 is equipped with a side air vent 19. The other end of spike 18 is enlarged and fits snugly into a drip chamber 22. Drip chamber 22 traps air contained in the set 14 and facilitates adjusting the flow rate of intravenous fluid 13 from container 12 as the flow proceeds drop wise. The outlet at the bottom of drip chamber 22 is connected to a first segment of tubing 23 which fits into agent formulator 30, the details of which are presented in FIGS. 2 and 3. A second segment of tubing 25 leads from agent formulator 30 to bacterial filter 27. A third segment of tubing 29 extends from filter 27 to an infusion agent receptor site, terminating in an adapter-needle assembly 28 that is inserted into a vein of a warm-blooded animal 20, shown as a human arm. A piece of tape 21 holds adapter-needle assembly 28 firmly in place on the recipient's arm. The administration set can also include a pair of tubing clamps 24 and 26 located on either side of formulator 30 which may be used to govern or stop the flow of intravenous fluid through the intravenous delivery system 10. Agent formulator 30, as seen in FIGS. 2 and 3, is the unique component of the intravenous delivery system 10. Agent formulator 30 comprises a wall 32 forming a chamber 34. At least a portion of the wall 32 is comprised of a material 36 which is permeable to the beneficial agent contained within, and delivered by, the delivery device 40. The wall portion 36 forms a "drug delivery window" within the otherwise impermeable wall 32 which may be formed of glass, plastic or the like. During delivery of beneficial agent from device 40, the flowing IV fluid 13 must be in contact with the interior surface of wall portion 36. Preferably, the entire chamber 34 remains filled with the flowing IV fluid 13.

The wall portion 36 may be comprised of known drug permeable and/or microporous materials which allow the beneficial agent delivered by device 40 to diffuse therethrough but which prevent convective IV fluid flow therethrough. The composition of wall portion 36 should be selected in accordance with the type of beneficial agent being delivered by device 40. In general, the wall portion 36 should be comprised of a polymeric composition that allows a drug or other beneficial agent delivered by device 40 to diffuse through wall portion 36 and into chamber 34. Representative polymers for forming wall portion 36 include olefin polymers, vinyl polymers, condensation polymers, addition polymers, rubber polymers and silicone polymers, and in particular, polyethylene, polypropylene, polyvinyl acetate, polyvinyl acetal, polyvinyl chloride, polyamides, polyesters, butadiene rubber, organo-silicone polymers and copolymers thereof.

When the device 40 delivers a hydrophilic drug, the wall portion 36 is preferably comprised of a hydrophilic or microporous material. Examples of suitable hydrophilic materials include polyurethanes, polyvinyl alcohols, polyamides and cellophane. Of these, polyurethanes and cellophane are most preferred. Suitable microporous materials are described below in connection with the delivery of polypeptides, proteins and other macromolecules.

When device 40 delivers a lipophilic drug, the wall portion 36 is preferably comprised of a lipophilic material. Examples of suitable lipophilic materials include natural rubbers, silicone rubbers, Hytrel ® (a thermoplastic polyester elastomer sold by E.I. DuPont de Nemours of Wilmington, Del.), ethylene vinyl acetate (EVA), polyvinyl chloride, and Kraton ® (a styrene-butadiene block copolymer sold by Shell Chemical Co. of Houston, Tex.). Of these, ethylene vinyl acetate copolymers, silicone rubbers and natural rubbers are preferred.

When device 40 delivers a polypeptide, protein or other macromolecule, the wall portion 36 is preferably comprised of a microporous material. The pores in the microporous material will generally have a size of less than about 0.2 microns, and preferably about 0.01 to 0.2 microns. Pores having the above recited size ranges are too small to allow bacterial cells to pass through the pores and can thereby maintain the sterility of the chamber 34. In general, microporous materials having pore sizes in the above mentioned range will allow water molecules from the parenteral fluid to diffuse into the membrane. In some cases, the exterior of the wall portions 11 and 36 will feel wet to the touch. However, microporous membranes having the above mentioned pore size ranges will be effective to prevent convective flow losses of water-based parenteral fluids through the wall portions 11 and 36. If necessary or desirable, the microporous wall portions 11 and 36 can be treated with a water non-wetting material to further reduce capillary IV fluid losses through the wall portions 11 and 36. In addition, the delivery device 40 may utilize a carrier which is immiscible in water. In such a case, the beneficial agent is suspended in a water-immiscible fluid carrier (e.g., an oil). When the oil-based carrier enters the pores of the microporous membrane, the pores will repel any water-based parenteral fluid which helps prevent convective losses through the wall portions 11 and 36.

Examples of suitable microporous materials include Celgardo ® (a microporous polypropylene film sold by Celanese Chemical Co. of Dallas, Tex.) cellophane, glass frits, vycor glass, porous glass and microporous membranes of the type utilized in known elementary osmotic pumps. Of these, porous glass is most preferred.

Selection of polymers for forming wall portion 36 for the passage of a drug therethrough can be determined by measuring the rate of diffusion through the polymeric wall material. Various techniques can be used to determine the permeability of a homopolymer, copolymer, or terpolymer to the passage of a drug. One method that can be used is to position a film of the polymer, of known thickness, as a barrier between a rapidly stirred, saturated solution of the drug and a rapidly stirred solvent bath (typically water), at a constant temperature, typically 25° C., and periodically measuring the concentration in the drug solution and in the solvent bath. Then, by plotting the drug concentration in the solvent bath versus time, the permeability coefficient, P, of the polymeric film may be determined from Fick's Law of Diffusion. Fick's Law of Diffusion is expressed by the following equation (I):

$$\text{Slope of plot} = (Q_2 - Q_1/t_2 - t_1) = PAC/h \qquad (I)$$

wherein:

$Q_1$ = cumulative amount of drug in the downstream solvent in micrograms at $t_1$;
$Q_2$ = cumulative amount of drug in solvent in micrograms at $t_2$;
$t_1$ = elapsed time to first sample, i.e., $Q_1$;
$t_2$ = elapsed time to second sample, i.e., $Q_2$;
A = area of film in $cm^2$;
C = concentration of drug in saturated solution; and
h = thickness of film in cm.

By determining the slope of the plot, i.e., $[Q_1 - Q_2/t_1 - t_2]$ and solving the equation using the known or measured values of A, C and h, the permeability coefficient, P, in $cm^2$/time of the film for a given drug is readily determined. The procedures used to determine the rate of release through the polymer can be ascertained easily by standard techniques known to the art as recorded in *J. Pharm. Sci.*, Vol. 52, pp. 1145–49, (1963); ibid, Vol. 53, pp. 798–802, (1964); ibid, Vol. 54, pp. 1459–1464, (1965); ibid, Vol. 55, pp. 840–843 and 1224–39, (1966); *Encyl. Polymer Sci. Technol.*, Vol. 5 & 9, pp. 65–82 and 794–807, (1986); the references cited therein, and the like.

Wall portion 36 may also optionally contain a plasticizer such as a member selected from the group consisting of phthalate ester, adipate ester, sebacate ester, azelate ester, di(2-ethylhexyl) phthalate, butyl phthalyl butyl glycolate, diamyl phthalate, dibutyl succinate, diethylene glycol dipropionate, glycerol monooleate, ethyl phthalyl ethyl glycolate, triethyl citrate, tributyl citrate, trialkyl citrates sold under the tradename Citroflex by Morflex Inc. of Greensboro, N.C., tributyl phosphate, triethylene glycol dibutyrate, glycol monooleate, polyethylene glycol 200; polyethylene glycol 400-monolaurate, diethyl lauramide, oleic and mineral oil, epoxidized soybean oil and the like. The amount of plasticizer in wall portion 36 is from about 5 weight percent (wt %) to 30 wt %, or more.

In an alternative embodiment of the invention, the agent permeable wall portion 36 may be formed in situ. For example, wall 32 of formulator 30 may be composed of a polymer, such as polyvinylchloride, a polyester or a polyurethane, which is initially impermeable to the passage of drug or agent. A portion 36 of wall 32 can be treated with a permeability enhancing agent, such as a plasticizer or a transdermal permeation enhancer, in order to form a drug permeable wall portion 36 in situ. The plasticizer may be delivered concurrently with the drug or agent from delivery device 40. For example, when the wall 32 is formed of polyvinylchloride, delivery device 40 contains both drug and a plasticizer of polyvinylchloride, such as phthalate ester. Upon delivery of the phthalate ester from device 40, the portion 36 which is immediately adjacent device 40 is plasticized and becomes drug permeable. Thereafter the drug is delivered from device 40 through wall portion 36 into chamber 34.

When the wall portion 36 is comprised of a material having poor rigidity and/or strength, it may be supported by a rigid porous or grid-like polymer structure (not shown in the figures) provided within chamber 34. The porous or grid-like polymer structure should allow the IV fluid to contact the interior surface of wall portion 36 to allow the beneficial agent to be delivered into the IV fluid. When the wall portion 36 is comprised of a fragile material or a material having poor tear strength, it may be necessary to provide a protective covering (not shown in the figures) over the wall portion 36. The protective covering can take any number of forms but in any event should be effective to prevent or minimize unnecessary stresses placed on the wall portion 36 and yet provide easy access to attach a drug delivery device 40 thereon.

In its broadest sense, the drug delivery device 40 comprises a beneficial agent-containing reservoir which can be releasably attached to the exterior surface of the wall portion 36. Typically, the reservoir comprises a polymeric matrix having a drug or other beneficial agent dispersed therein. The reservoir may be releasably attached to the wall portion 36 using tape, clamps, adhesives or other conventional attaching means. Mechanical attaching means are preferred when the beneficial agent delivered by the device is incompatible with adhesives. In cases where the beneficial agent is adhesive-compatible, the reservoir preferably incorporates a releasable contact adhesive, or has a releasable contact adhesive layer coated on one side thereof, so that the reservoir is itself releasably adhered to the wall portion 36.

The agent delivery device 40 used in the present invention is not limited to any particular type or structure. Many suitable devices are known in the art and have generally been used in applications wherein a drug or other beneficial agent is administered transdermally. Examples of suitable agent delivery devices 40 may be found for example in U.S. Pat. Nos. 3,536,809; 3,598,122; 3,598,123; 3,787,571; 3,699,963; 3,731,683; 3,734,097; 3,742,951; 3,797,494; 3,964,482; 3,996,934; 4,031,894; 4,060,084; and others to name just a few. The teachings of the above listed patents concerning the relevant structures of the drug delivery devices and the particular drugs which may be suitably administered using these devices are incorporated herein by reference.

Figure 4:
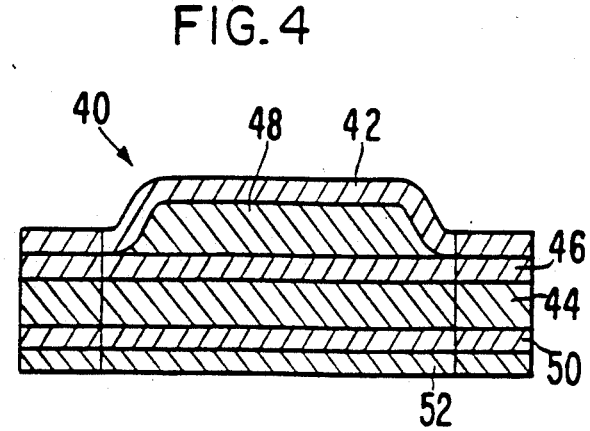
FIG. 4 is a detailed sectional view of a preferred drug delivery device 40 which is adapted to be attached to formulator 30 as shown in FIGS. 1-3.

A preferred drug delivery device 40 is illustrated in FIG. 4. Device 40 is a multilaminate system comprised of an impermeable backing layer 42, a drug reservoir 48 and an adhesive layer 50. Device 40 also includes a permeation enhancer-containing layer 44 (e.g., an ethanol gel layer) and a rate controlling membrane 46. A strippable release liner 52, adapted to be removed prior to application, is normally included in the packaged product.

The drug reservoir 48 may be comprised of a polymeric matrix or carrier having the drug/beneficial agent to be delivered, dispersed throughout. The polymer matrix stores and releases the beneficial agent/drug by diffusion or by osmotic action to wall portion 36. Representative polymers for forming the matrix may be selected from homopolymers, copolymers, cross-linked polymers, diffusion polymers and microporous polymers. Examples of suitable polymers include acrylic polymers and copolymers of methacrylate, ethylacrylate, ethylmethacrylate, and methylmethacrylate; homopolymers and copolymers including vinylchloridevinylacetate copolymer; chlorinated vinyl chloride; polyethylene; polypropylene; ethylene-propylene copolymer; chlorinated polyethylene; ethylene-vinyl-acetate copolymer (EVA) of the type described in U.S. Pat. No. 4,144,317; styrene-butadiene copolymer; acrylonitrile-styrene-butadiene terpolymer; polyvinylidene chloride; vinylchloride-acrylonitrile copolymer; vinylchloride-vinylidene chloride copolymer; vinylidenechloride-acrylate ester copolymer; polybutylene terephthalate; vinylchloride-acrylate ester copolymer; cross-linked polyvinyl acetals such as cross-linked polyvinyl formal; cross-linked polyvinyl acetal and cross-linked polyvinyl butyryl; polyethers; polyesters; sparingly cross-linked polyesters; polyurethane; polyamide; chlorosulfonated polyolefins; polyolefins; polybutadiene; polyisoprene; polysilicone; natural and synthetic rubbers; and the like. The polymers are known in *The Handbook of Common Polymers,* by Scott et al., (1971), published by CRC Press, Cleveland OH; in *Modern Plastics Encylopedia,* (1979), published by McGraw-Hill Inc., New York, N.Y.; and in *Handbook of Plastics and Elastomers,* by Harper, (1976), published by McGraw-Hill Inc., San Francisco, Calif.

The drug reservoir 48 may contain the drug alone or it may contain the drug along with one or more permeation enhancers. The drug/beneficial agent should either itself be soluble in the parenteral fluid or capable of being solubilized using adjuvants such as surfactants and/or co-ions. The amount of drug in the reservoir 48 will depend upon the rate at which the drug is delivered from the system and the intended duration of therapy. The amount of drug/beneficial agent in reservoir 48 generally will be about 0.1% to 80% by weight, with a more preferred amount of 5% to 50% by weight. The device 40 can be manufactured for delivering beneficial amounts of a drug over a prolonged period from about 0.5 hours to several days or longer, with a more preferred period of about 4 to 50 hours. The device 40 used in the present invention releases from 10 ng to 750 mg per hour, or higher. The reservoir 48 may also include diluents, stabilizers, vehicles, gelling agents, and the like.

The backing member 42 serves the purpose of insuring unidirectional passage of drug through wall portion 36 into chamber 34, and also of providing support for the system, where needed. The backing layer can be flexible or nonflexible and suitable materials include, without limitation, cellophane, cellulose acetate, ethylcellulose, plasticized vinylacetate-vinylchloride copolymers, polyethylene terephthalate, nylon, high and low density polyethylene, polypropylene, metalized polyester films, polyvinylidene chloride, coated flexible fibrous backings such as paper and cloth and aluminum foil. Such backings can be in the form of precast films or fabrics which are bonded to the reservoir by heat or adhesives and can be coated onto the reservoir 48.

The device 40 is held in place on wall portion 36 by means of an in-line pharmaceutically acceptable contact adhesive layer 50. Drug and/or a permeation enhancer may also be incorporated into the adhesive layer 50. The composition and thickness of the adhesive layer 50 are preferably such that it does not constitute a significant permeation barrier to the drug or the permeation enhancer, if one is present. Any pharmaceutically acceptable contact adhesive may be used. Representative adhesives include mixtures of 2-cyanoacrylate and dimethyl methylenemalonate, monomeric ester of alpha-cyanoacrylic acid, cross-linked copolymer of dimethylaminoethylmethacrylate and an alkyl acrylate, adhesive compositions comprising a hydrocolloid gum, polyisobutylene and cross-linked dextran, silicone medical adhesives, mineral oil-polyisobutylene adhesives, contact adhesives such as those disclosed in U.S. Pat. Nos. 3,797,494 and 4,031,894, and the like. The adhesive optionally can contain a rheological agent that imparts thixotropic characteristics to the adhesive, aids in increasing its cohesiveness and bond strength, imparts slump control, maintains the delivery device 40 in contact with wall portion 36, and lets it be easily removed therefrom at the end of the delivery period. The rheological agents useful for this purpose are silicone compounds such as fumed silica.

The adhesive may also optionally contain a surfactant which allows better contact between the surface of the delivery device 40 and the exterior surface of wall portion 36.

If necessary or desirable, known permeation enhancers, such as ethanol or glycerol monolaurate, may be contained either within the separate layer 44 (if one is present), in the adhesive layer 50, in the drug reservoir 48, or in any combination of these.

Most preferably, device 40 includes a rate controlling membrane 46 which is effective to control the rate at which the beneficial agent is delivered from reservoir 48 into chamber 34. When device 40 contains a rate controlling membrane 46, the wall portion 36 should provide minimal resistance to drug flux. The rate controlling membrane 46 may be comprised of permeable, semipermeable or microporous materials which are known in the art to control the flux rate of the drug out of the device 40. Suitable materials include polyvinylacetate and ethylene vinylacetate polymers. When a rate controlling membrane 46 is present in device 40, the beneficial agent delivery rate is determined by the delivery device 40, and not by the wall portion 36.

However, it is also within the scope of the present invention to utilize a delivery device 40 containing no rate controlling membrane 46. When no rate controlling membrane 46 is provided in delivery device 40, the wall portion 36 should be comprised of a material which is effective to control the rate at which the beneficial agent is delivered into chamber 34. When the wall portion 36 itself controls the rate at which the beneficial agent is delivered into chamber 34, the formulator 30 will be relatively drug specific (i.e., the formulator will only be suitable to control the rate of delivery of a specified drug or class of drugs.

On the other hand, when the wall portion 36 provides minimal resistance/control over the drug flux therethrough, the formulator 30 can be used with a wide range of drugs. However, in this second configuration, the control of drug delivery should be provided by the drug delivery device 40. This is preferred since transdermal type drug delivery-devices are generally manufactured to deliver a specific drug at a specific drug delivery rate.

The size (e.g., the surface area of adhesive layer 50 which is in contact with wall portion 36) of the device 40 can typically vary from less than 1 $cm^2$ to greater than 200 $cm^2$. An average device 40 however, will typically have a size within the range of about 5-50 $cm^2$.

Embodiments of device 40 in which the drug and permeation enhancer supplies are separate (such as that illustrated in FIG. 4) may be advantageous or necessary in instances where formulation or storage of the drug and the enhancer in contact with each other is impractical or undesirable or where separation of the drug and the enhancer facilitates selection of the rate controlling membrane.

Although the dimensions of formulator 30 need not be within any specified ranges, the volume of chamber 34 is preferably kept to a minimum in order to minimize the dead volume within administration set 14. Likewise, the size (i.e., the surface area) of wall portion 36 should be large enough to accommodate at least one delivery device 40, and preferably large enough to accommodate two or more delivery devices 40. By making wall portion 36 large enough to accommodate a plurality of the delivery devices 40, it is possible to simultaneously deliver more than one beneficial agent into the IV fluid 13 flowing through chamber 34. Likewise, it is also possible to deliver a single beneficial agent at a delivery rate which is a multiple (e.g., $2\times, 3\times, 4\times$, etc.) of the delivery rate achieved by a single delivery device 40 (e.g., by adhering 2, 3, 4, etc. identical devices 40 to wall portion 36).

Important advantages achieved by the formulator 30 of the present invention include (1) easy adjustment of the beneficial agent delivery rate, (2) easily changing the type of beneficial agent delivered, (3) it is unnecessary for a nurse or a pharmacist to preformulate the drug or other beneficial agent and (4) the drug or other beneficial agent has a longer stable shelf-life since the drug is in solid form, rather than in solution. For instance, if it is desired to increase the rate of delivery of a beneficial agent (e.g., an antibiotic) into the flowing IV fluid 13, one can simply select a suitable antibiotic delivery device 40 with a specified delivery rate. Furthermore, if it is desired to either double, triple or quadruple the delivery rate of this particular antibiotic, it is only necessary to apply 2, 3, or 4 delivery devices 40, respectively, to the wall portion 36.

Likewise, if instead of delivering an antibiotic it is desired to deliver an anti-cancer agent into the flowing IV fluid, it is only necessary to remove the antibiotic-containing drug delivery device 40 and replace it with an anti-cancer drug-containing delivery device.

Because the agent delivery devices 40 are attached to the exterior surface of formulator 30, there is no danger of contamination of the flowing IV fluid. Thus, changing the type of drug delivered or the drug delivery rate does not require time consuming sterilization procedures. This is especially important when utilizing devices which deliver protein formulations since proteins are sensitive to heat sterilization and have a tendency to denature when heated. Furthermore, protein formulations are more stable in solid form than in solution. Thus, the agent delivery device 40 (which maintains the protein formulation in solid form) has improved stability and longer shelf life compared to standard IV protein solutions.

The invention is further illustrated by the following examples.

EXAMPLE I

A nitroglycerin ("NG")/triethyl citrate reservoir composition comprising a silicone medical fluid carrier gelled with silica, having NG on lactose uniformly dispersed therethrough and triethyl citrate (Citroflex A6, sold by Morflex Inc. of Greensboro, N.C.) absorbed in a particulate carrier is fabricated by placing 5 kg of silicone medical fluid having a viscosity of about 100 centistokes and 175 grams of colloidal silicon dioxide in a high energy mixing vessel and blending to produce a gelled silicone fluid. 200 Grams of Accurel ® porous polypropylene available from ARMAK Company is placed in a separate vessel and approximately 1200 grams of Citroflex A6 is added with stirring to produce an essentially dry flowable powder which on visual observation appears to have absorbed substantially all of the Citroflex. 5 kg of nitroglycerin-lactose (10 wt % nitroglycerin) and the Citroflex loaded porous polypropylene is placed in the original high energy mixing vessel and mixed until a homogeneous blend is obtained. A form-fill-seal pouching machine is used to pouch the NG-Citroflex gel so formed between an impermeable backing member comprising a medium density polyethylene/aluminized polyester/ethylene vinyl acetate multilaminate (Medpar ® 1006 available from Minnesota Mining & Manufacturing Company) peripherally thermosealed to the rate controlling membrane layer of a trilaminate film consisting of a release liner layer formed from polyester film coated with a film release agent, an adhesive layer formed of silicone medical adhesive and a release rate controlling membrane layer formed from a 1 mil thick ethylene vinyl acetate (12% VA) membrane. Devices are fabricated having an NG/Citroflex releasing surface area of approximately 5 cm$^2$.

One of the devices is adhered to an IV drug formulation chamber formed of polyvinylchloride. The wall thickness of the drug formulation chamber is 5 mils. The drug formulation chamber has a substantially flat surface to which the drug delivery device is applied. Once the drug delivery device is attached to the wall of the drug formulation chamber, the device delivers Citroflex A6 into the polyvinylchloride wall. Citroflex A6 is a plasticizer for polyvinylchloride. After a period of time, the portion of the chamber wall which is immediately adjacent to the drug delivery device becomes plasticized and drug permeable. Thereafter, nitroglycerine is delivered by the device through the drug permeable wall portion and into the IV fluid within the drug formulation chamber.

EXAMPLE II

A monolithic transdermal device is prepared by melt blending 33 parts ethylene vinyl acetate (40% VA) with 32 parts Staybelite Ester No. 5, 5 parts estradiol valerate and 25 parts triethyl citrate (Citroflex A4 sold by Morflex Inc. of Greensboro, N.C.). The mixture is extruded and calendared to a thickness of 12 mils between an occlusive backing film of the type described in Example I and a strippable release liner film. Individual devices are rotary die cut with an area of 50 cm$^2$.

One of the devices is adhered to an IV drug formulation chamber formed of polyvinylchloride. The wall thickness of the drug formulation chamber is 5 mils. The drug formulation chamber has a substantially flat surface to which the drug delivery device is applied. Once the drug delivery device is attached to the wall of the drug formulation chamber, the device delivers Citroflex A4 into the polyvinylchloride wall. Citroflex A4 is a plasticizer for polyvinylchloride. After a period of time, the portion of the chamber wall which is immediately adjacent to the drug delivery device becomes plasticized and drug permeable. Thereafter, estradiol valerate is delivered by the device through the drug permeable wall portion and into the IV fluid within the drug formulation chamber.

Other benefits and advantages of the invention will become apparent to those skilled in the art. While the preferred embodiments of the invention have been selected for illustration in the drawings and have been described in detail herein, those skilled in the art will appreciate that the drug formulation chamber 30 having the drug delivery window 36 may be used in applications other than the illustrated IV administration set. Broadly, the formulation chamber 30 may be used in any system used to deliver a fluid parenterally to an animal. For example, the drug formulation chamber 30 may be used in the delivery line of a portable infusor pump. Those skilled in the art will appreciate other uses for the drug formulation chamber 30 described herein, and further that various modifications, changes, additions and omissions from the illustrated embodiments can be made without departing from the spirit and scope of the invention, as defined in the appended claims.

I claim:

1. An agent formulator for use in a parenteral fluid delivery system, the formulator comprising:

(a) a chamber having a fluid inlet means connectable to a reservoir of a parenterally acceptable fluid and a fluid outlet means to maintain a continuous flow of the parenteral fluid therethrough, the chamber having a wall, at least a portion of the wall being comprised of a material that is impermeable to a beneficial agent to be delivered into the parenteral fluid flowing through the chamber, the wall portion having an interior surface and an exterior surface which is accessible from the exterior of the formulator; and (b) a transdermal type agent delivery device attached to the exterior surface of the wall portion, the delivery device comprising a reservoir containing the beneficial agent and a reservoir containing an agent which renders the wall portion permeable to the beneficial agent, the device being releasably attached to the exterior surface of the wall portion;

wherein in operation, the permeability enhancing agent is delivered to the wall portion and renders the wall portion permeable to the beneficial agent, but impermeable to convective flow of the parenteral fluid therethrough, the fluid flowing through the chamber contacts the interior surface of the wall portion, causing the beneficial agent to be delivered from the device through the permeable wall portion and into the flowing fluid.

2. The formulator of claim 1, wherein the delivery device comprises a laminate including: a backing member, adhesive surface adapted to releasably adhere to the exterior surface of the wall portion.

3. The formulator of claim 1, wherein the delivery device contains a drug and the chamber contains an intravenously acceptable fluid.

4. The formulator of claim 1, wherein the wall portion is composed of a material which controls the rate at which the agent is delivered into the fluid flowing through the chamber.

5. The formulator of claim 1, wherein the delivery device contains a membrane layer which controls the rate at which the beneficial agent is delivered into the fluid flowing through the chamber.

6. The formulator of claim 1, wherein said chamber contains an air release vent and is simultaneously employed as a drip chamber for providing a measurable number of drops per minute of the fluid, the fluid transporting the agent delivered by the delivery device to an agent receptor site.

7. The formulator of claim 1, wherein the wall portion is composed of a material which controls the rate at which the agent is delivered into the chamber.

8. The formulator of claim 1, wherein the reservoir containing the permeability enhancing agent and the reservoir containing the beneficial agent are one and the same.

9. The formulator of claim 1, wherein the permeability enhancing agent comprises a plasticizer of the material forming the chamber wall.

10. The formulator of claim 1, wherein the wall portion is comprised of polyvinylchloride and the permeability enhancing agent comprises triethyl citrate.

11. The formulator of claim 1, including a plurality of agent delivery devices attached to the exterior surface of the wall portion.

12. The formulator of claim 1, wherein the delivery device is releasably adhered to the wall portion.

13. The formulator of claim 1, wherein the beneficial agent is osmotically active.

14. The formulator of claim 1, wherein the beneficial agent comprises a drug and an osmotically active solute.

15. A parenteral delivery system for administering an agent parenterally to an animal in which the agent is formulated in situ, the delivery system including a container of pharmaceutically acceptable parenteral fluid that is a carrier for the agent, a parenteral fluid administration set connected to the container for permitting the fluid to flow from the container through the administration set to the animal, the administration set including a drip chamber, tubing extending from the drip chamber to the animal, and an agent formulator chamber connected to the tubing such that the intravenous fluid flows through the formulator, the formulator comprising:

(a) a chamber having a fluid inlet means connected to said reservoir of parenterally acceptable fluid by said tubing and a fluid outlet means coupled to said animal by said tubing to maintain a continuous flow of said parenteral fluid therethrough, the chamber having a wall at least a portion of the wall being comprised of a material that is impermeable to the beneficial agent to be delivered into the parenteral fluid flowing through the chamber, the wall portion having an interior surface and an exterior surface which is accessible from the exterior of the formulator; and b) a transdermal type agent delivery device attached to the exterior surface of the wall portion, the delivery device comprising a reservoir containing the beneficial agent and a reservoir containing an agent which renders the wall portion permeable to the beneficial agent, the device being releasably attached to the exterior surface of the wall portion;

wherein operation, the permeability enhancing agent is delivered to the wall portion and renders the wall portion permeable to the beneficial agent, but impermeable to convective flow of the parenteral fluid therethrough, the fluid flowing through the chamber contacts the interior surface of the wall portion, causing the beneficial agent to be delivered from the device through the permeable wall portion and into the flowing fluid.

16. The parenteral delivery system of claim 15, wherein a skin piercing means is connected to the tubing for administering the agent to the animal.

17. The parenteral delivery system of claim 15, wherein the animal is a human and the delivery device contains a drug.

18. The parenteral delivery system of claim 15, wherein the delivery device is releasably adhered to the external surface of the wall portion.

19. A method for the controlled parenteral administration of a beneficial agent to an animal, which method comprises:
(a) admitting into the animal a parenteral fluid administration system, the system including;
  (1) a container of a pharmaceutically acceptable parenteral fluid that is a carrier for the agent;
  (2) an agent formulation chamber having an inlet that communicates with the container to permit the fluid to flow from the container into the chamber, and an outlet that communicates with the animal to permit the fluid to flow from the chamber into the animal, the chamber also having a wall portion that is impermeable to the agent, the wall portion having an interior surface and an exterior surface which is accessible from the exterior of the formulation chamber; and
(b) releasably attaching a transdermal-type agent delivery device (40) to the exterior surface of the wall portion, the delivery device including a reservoir containing the beneficial agent and a reservoir containing an agent which renders the wall portion permeable to the beneficial agent;
wherein in operation the permeability enhancing agent is delivered to the wall portion and renders the wall portion permeable to the beneficial agent, but impermeable to convective flow of the parenteral fluid therethrough, the fluid flowing through the chamber contacts the interior surface of the wall portion, causing the beneficial agent to be delivered from the device through the permeable wall portion and into the flowing fluid, thereby administering the beneficial agent to the animal in a beneficially effective amount over a prolonged period of time.

20. The method of claim 19, wherein the wall portion is composed of a material which controls the rate at which the beneficial agent is released into the fluid flowing through the chamber.

21. The method of claim 19, wherein the beneficial agent is released at a rate which is controlled substantially by a membrane layer in the delivery device.

22. The method of claim 19, wherein the animal is a human and the beneficial agent is a drug.

23. The method of claim 19, wherein the reservoir containing the permeability enhancing agent and the reservoir containing the beneficial agent are one and the same.

24. The method of claim 19, wherein the permeability enhancing agent comprises a plasticizer of the material forming the wall.

25. The method of claim 24, wherein the wall portion is comprised of polyvinylchloride and the permeability enhancing agent comprises triethyl citrate.

26. A method for the controlled parenteral administration of a beneficial agent to an animal, which method comprises:
(a) admitting into the animal a portion of a parenteral fluid administration system, the system comprising:
  (1) a container of a pharmaceutically acceptable parenteral fluid that is a carrier for the agent;
  (2) an agent formulation chamber having an inlet that communicates with the container to permit the fluid to flow from the container into the chamber, and an outlet that communicates with the animal to permit the fluid to flow from the chamber into the animal, the chamber also having a wall portion that is permeable to the agent; and
(b) releasably attaching an agent delivery device to an accessible exterior surface of the wall portion, which wall portion is initially impermeable to the agent, the delivery device including a reservoir containing the beneficial agent and a plasticizer of the material forming the wall portion;
wherein in operation, the wall portion is made permeable to the agent by contact with the permeability enhancing agent and the fluid flowing through the chamber contacts an interior surface of the wall portion, causing the agent to be delivered from the device through the wall portion and into the flowing fluid, thereby administering the agent to the animal in a beneficially effective amount over a prolonged period of time.

27. The method of claim 26, wherein the agent is released at a rate which is controlled substantially by the wall portion and which is substantially independent of volumetric flow rate of the fluid flowing through the chamber.

28. The method of claim 26, wherein the agent is released at a rate which is controlled substantially by a membrane layer in the delivery device.

29. The method of claim 26, wherein the animal is a human and the agent is a drug.

30. The method of claim 26, wherein the plasticizer is delivered to the wall portion by the agent delivery device.

31. The method of claim 26, wherein the plasticizer is selected from the group consisting of phthalate ester, adipate ester, sebecate ester, azelate ester, di(2-ethylhexyl) phthalate, butyl phthalyl butyl glycolate, diamyl phthalate, dibutyl succinate, diethylene glycol diproprionate, glycerol monooleate, ethyl phthalyl ethyl glycolate, tributyl phosphate, triethylene glycol dibutyrate, glycol monooleate, polyethylene glycol 200, polyethylene glycol 400-monolaurate, diethyl lauramide, oleic and mineral oil, epoxidized soybean oil, trialkyl citrates, and mixtures thereof.

32. The method of claim 31, wherein the plasticizer comprises a trialkyl citrate.

33. The method of claim 32, wherein the plasticizer comprises triethyl citrate.

34. The method of claim 26, wherein the wall portion is comprised of polyvinylchloride and the plasticizer comprises triethyl citrate.

* * * * *

UNITED STATES PATENT AND TRADEMARK OFFICE
CERTIFICATE OF CORRECTION

PATENT NO. : 5,250,028
DATED : Oct. 5, 1993
INVENTOR(S) : Felix Theeuwes; Su I. Yum It is certified that error appears in the above-indentified patent and that said Letters Patent is hereby corrected as shown below:

In column 13, line 50, after the word "member" insert --a middle reservoir containing the beneficial agent, and an--.

Signed and Sealed this

Twenty-third Day of August, 1994

Attest:

BRUCE LEHMAN

Attesting Officer

Commissioner of Patents and Trademarks